United States Patent [19]
Ballinger, Jr.

[11] Patent Number: 5,885,604
[45] Date of Patent: Mar. 23, 1999

[54] METHOD FOR PROTECTING SEEDS FROM BIRDS

[75] Inventor: Kenneth E. Ballinger, Jr., Kennett Square, Pa.

[73] Assignee: DuPont Conagra, Wilmington, Del.

[21] Appl. No.: 918,800

[22] Filed: Aug. 26, 1997

[51] Int. Cl.⁶ ..................................... A01N 25/26

[52] U.S. Cl. .......................... 424/405; 424/406; 424/407; 424/409; 424/410; 514/920; 514/680; 504/100

[58] Field of Search ..................... 504/100, 101; 424/403, 405–407, 409, 410; 514/920, 680, 683, 690

[56] References Cited

U.S. PATENT DOCUMENTS 5,464,625  11/1995  Nolte et al. .............................. 424/405

FOREIGN PATENT DOCUMENTS 62-43961   9/1987  Japan .
1601226   10/1981  United Kingdom .

Primary Examiner—Neil S. Levy

[57] ABSTRACT

A method for deterring birds from damaging planted seeds by applying to the seeds before planting or to the surface of the ground overlying the planted seeds a non-toxic solid coating material which (1) is repellent to the taste of birds and (2) absorbs light having a wave length within the range of 300–400 nm.

14 Claims, 1 Drawing Sheet

METHOD FOR PROTECTING SEEDS FROM BIRDS

FIELD OF INVENTION

The invention is directed to a method for protecting plant seeds from birds. More particularly, it is directed to a method for coating seeds with an agent which repels birds from scattering and eating the seeds.

BACKGROUND OF THE INVENTION

One of the ongoing problems of agriculturists, such as farmers and gardeners, is the loss of planted seeds to the forays of various seed-eating birds. The financial loss from such bird theft is two-fold: (1) the loss of plant yields and (2) the cost of replacing the seeds. This kind of seed loss is ubiquitous in that it is experienced with virtually all cereal seeds and the majority of flower and other garden seeds. It is not practicable or safe to coat seeds with poisons because of the danger to less prevalent wild animal species and domestic animals. Therefore, there exists a long-felt need for a way safely to treat seeds so that birds are not attracted to them as food.

PRIOR ART

Japanese patent 62-43961 discloses that 9,10-anthraquinone has been used as a coating on both crop and garden plant seeds to repel birds therefrom and is directed to the use of various soluble anthrahydroquinones as a bird-repellent coating on seeds.

SUMMARY OF THE INVENTION

In its most general aspect, the invention is directed to a method for deterring birds from damaging planted seeds comprising applying to the seeds a non-toxic coating of a taste-repellent material which absorbs light having a wave length of 300–400 nm.

In a first aspect, the invention is directed to a method for deterring birds from damaging planted seeds comprising applying to the unplanted seeds a solid coating composition which is comprised of a non-toxic material which (1) absorbs light having a wave length of 300–400 nm and (2) is a deterrent to birds because of its taste.

In a further aspect, the invention is directed to a method for deterring birds from damaging planted seeds by the above-described method in which the taste repellent material is a polycyclic quinone or precursor thereof, which absorbs light having a wave length of 300–400 nm.

In a still further aspect, the invention is directed to a method for deterring birds from damaging planted seeds comprising applying to the surface of the ground above the planted seeds a particulate coating of polycyclic quinone or precursor thereof, which absorbs light having a wave length of 300–400 nm.

When using polycyclic quinones as the UV-absorbing material, the polycyclic quinone can be applied directly in the form of a liquid dispersion of the solid polycyclic quinone particles or it can be applied as an alkaline solution of polycyclic quinone precursor which is converted to particulate polycyclic quinone form upon exposure to air.

BRIEF DESCRIPTION OF THE DRAWING

The Drawing consists of FIGS. 1(a) through (e) in which various particulated forms of polycyclic quinone active material are depicted schematically in their application to seeds.

DETAILED DESCRIPTION OF THE INVENTION

A. Introduction

Figure 1A:
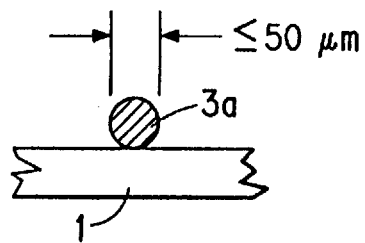

Many kinds of wildlife use visual cues to identify food in the environment in a manner similar to humans. Most species of animals use both long distance vision and close visual inspection to recognize food. In the case of birds, however, the visual acuity is much different than that of humans. Humans are capable of sensing light having a wave length in the single range of 400 to 700 nm. However, birds can see light in two visual spectra simultaneously. In particular, birds can detect light in the wave length ranges of 500–700 nm as well as 300–400 nm. Thus, birds can identify food which reflects light in the far ultra violet range, which is invisible to humans, down to the limits of the sun's UV radiation at the earth's surface.

Utilizing these principles, applicant has determined that a broad class of polycyclic quinones, which absorb light in various wave lengths within the range of 300–400 nm and which have taste repellency properties are particularly effective to repel birds from feeding on a wide variety of plant seeds.

It is not necessary that the light-absorbing materials absorb light throughout the range of 300–400 nm. It is sufficient that the material absorb a narrow band of light within that range sufficient to bring about a visually detectable shift in color perception by the bird. Thus, even if a narrow wave length-absorbing material is used, the seed is nevertheless distinctly marked by the resultant shift in the color of the coated seed as perceived by the bird.

It is believed that the bird is not deterred by the color shift alone. Instead, it appears that the bird first tastes the material coating the seeds. Upon finding the taste unsatisfactory, the bird thereafter avoids the material by visual identification of its distinct color. The total repellency effect of the compositions of the invention is therefore based on both taste and visual detection. In its broadest aspect, the invention is therefore directed to the use of non-toxic organic materials, which absorb light within the range of 300–400 nm, as a coating on seed surfaces.

B. Polycyclic Quinones

1. Composition: A wide variety of polycyclic quinones can be used in the invention. As used herein, the term "polycyclic quinone" refers to bicyclic, tricyclic and tetracyclic condensed ring quinones and hydroquinones, as well as precursors thereof. On the whole, the non-ionic polycyclic quinones and polycyclic hydroquinones (herein referred to collectively as PCQs) have very low solubility in water at ambient temperatures. For use in the invention, it is preferred that such PCQs have a water solubility no higher than about 1,000 ppm, by weight.

However, as noted above, certain precursors of such PCQs can also be used in the invention either combined with the relatively insoluble PCQs or by themselves. Such precursors are anionic salts of PCQs which are water soluble under alkaline anaerobic conditions. However, these materials are not stable and are easily converted to the insoluble quinone form upon exposure to air. Thus, when anionic PCQs are applied to plants and exposed to air, they are quickly changed to the water-insoluble, more active quinone form.

Among the water-insoluble PCQs which can be used in the invention are anthraquinone, 1,2-dihydroxy anthraquinone, 1,4-dihydroxy anthraquinone, naphthoquinone, anthrone(9,10-dihydro-9-oxo-anthracene), 10-methylene-anthrone, phenanthrenequinone and the alkyl, alkoxy and amino derivatives of such quinones, 6,11-dioxo-1H-anthra[1,2-c]pyrazole, anthraquinone-1,2-naphthacridone,7,12-dioxo-7,12-dihydroanthra[1,2-b]pyrazine, 1,2-benzanthraquinone, 2,7-dimethylanthraquinone, 2-methylanthraquinone, 3-methylanthraquinone, 2-aminoanthraquinone and 1-methoxyanthraquinone. Of the foregoing cyclic ketones, anthraquinone and 1,4-dihydroxyanthraquinone are preferred because they appear to be more effective. Naturally occurring anthraquinones can be used as well as synthetic anthraquinones.

Other PCQs which can be used include insoluble anthraquinone compounds such as 1,8-dihydroxy-anthraquinone, 1-amino-anthraquinone, 1-chloro-anthraquinone, 2-chloro-anthraquinone, 2-chloro-3-carboxyl-anthraquinone and 1-hydroxyanthraquinone. Various ionic derivatives of these materials can be prepared by catalytic reduction in aqueous alkali.

In addition, a wide variety of anthrahydroquinone compounds can be used in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4*a*,9*a*-tetrahydroanthrahydroquinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9–10) will result in the formation of the insoluble molecular anthrahydroquinone. Aerobic solutions will incur oxidation of the anthrahydroquinones to anthraquinone. Thus, anthrahydroquinones will not exist for long periods of time in an aerated environment such as that which is experienced by spraying. For these reasons, anthrahydroquinone treatments are usually implemented with the soluble ionic form in a caustic solution. Sodium hydroxide solutions are preferred over the hydroxides of other alkali metals for economic reasons.

2. Configuration: The PCQ used should be in physical form small enough to be touched by the sensory organs of the bird. That is, if the particles are too large, the taste sensors may pick up the taste poorly, if at all. Thus, for the PCQ to be more effective as a repellent, it is preferred to be of sufficiently small particle size that its taste can be sensed. Thus, the more effective quantity of repellent in any application is that which is in a form accessible to the birds' tongues; that is, it should be of sufficiently small size that it can be tasted.

Generally, because of these criteria, particles larger than about 50 micrometers cannot be adequately sensed and particles no larger than 30 micrometers are preferred. Similarly, smooth continuous surfaces of PCQ cannot be adequately sensed; and, of course, if the PCQ is coated with anything which is non-repellent to the bird or to which the bird is taste insensitive, the PCQ is ineffective. Though, strictly speaking, for the PCQ to be effective as a repellent it does not have to be in the form of discrete particles, nevertheless, the particles must be of sufficient size or have a contour that contains areas that are taste-accessible. This criterion is illustrated in the Drawing.

Figure 1B:
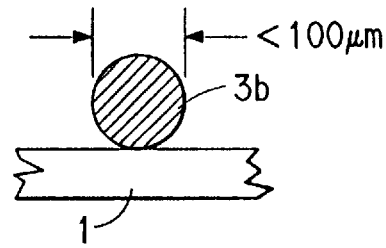
Figure 1C:
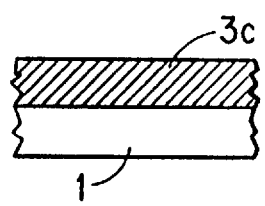
Figure 1D:
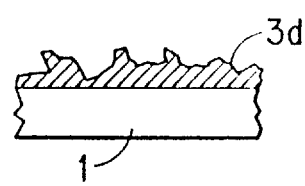
Figure 1E:
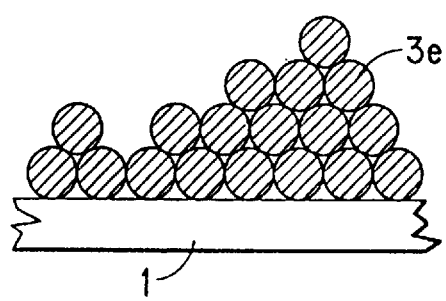

The particle in FIG. 1(*a*) would be accessible because it is sufficiently small. The particle in FIG. 1(*b*) would be less effective because it is too large to be sensed effectively. The smooth continuous coating in FIG. 1(*c*) would create little or no taste sensation because the large continuous surface would not have adequate access to the birds' taste sensors. On the other hand, the continuous coating shown in FIG. 1(*d*) would create at least moderate taste sensation because the protrusions on the coating are sufficiently small to be tasted. In this situation, the PCQ in the protrusions would be effective, but the PCQ in the main body of the coating would be less so, if at all. When the particles are portrayed as stacks of particles, as in FIG. 1(*e*), it can be seen that some of the particles in the upper layers would be accessible and therefore would be effective; but those particles in the lower layer would be less accessible and therefore less effective. The foregoing analysis shows clearly that the efficacy of the repellent is a function of both its configuration and accessibility. In turn, it can be seen that these variables are in large part dependent on the method of application.

When the PCQ is applied directly in particulate form, the size of the particles can be readily controlled. When such particles are applied as a single layer of particles, substantially all of the PCQ would be effective. However, if the particles are applied as a multiple of particle layers, essentially only the top layer would be effective. An important aspect of this analysis is that it is not important that the PCQ be applied as continuous covering. To the contrary, it is better that the coating of PCQ particles be discontinuous, at least on a micro scale, to enable functional exposure of the stomata of the foliage. Thus, the particles to be effective must be "particulated" in the sense that they contain areas which are accessible to the insects' taste apparatus.

3. Physical Properties - - - Volatility Water Solubility:

It is important to the effectiveness of the invention that the PCQ, in whatever physical form it is applied, be persistent. That is, the applied active material must be able to resist erosion by wind and rain and other environmental forces to which the treated surface is exposed. For this reason, it is preferred (1) that the active form of the PCQ have a relatively low solubility in water so that it is not easily washed off the treated plant surfaces, and (2) that it have a relatively high melting temperature so that it does not undergo excessive evaporation from the treated seed surfaces during exposure to high ambient temperatures. For these reasons, it is preferred that the active PCQ material has a solubility in water under ambient temperature conditions of no more than about 1000 ppm and preferably in the range of 200–1000 ppm. The melting temperature of the active PCQ component should be at least about 150° C. and preferably at least 200° C.

Even when the active PCQ material possesses the above-described preferred physical properties, the material may have poor persistence because it does not adhere well to the plant surface to which it is applied. This is a function of the different surface properties of the seed and the PCQ material. When this occurs, it is further preferred that the formulation contain a "sticking agent", i.e., a material which itself has good adhesion to the substrate and when mixed with the active material causes the PCQ to adhere to the substrate more firmly. Preferred sticking agents are aqueous polymer lattices, which upon evaporation of the water therefrom, form a polymeric mass which is highly adhesive to the plant surface and holds particles of the active material firmly on the plant surface. Such latex sticking agents typically contain a small amount of surfactant dissolved in the aqueous phase.

A distinct advantage of the PCQ compounds which have been tested for use in the invention is that they are essentially non toxic, i.e., they have an $LD_{50}$ of at least 2,000 mg/kg in orally administered female rats and preferably an $LD_{50}$ in rats of 5,000 mg/kg or higher. Because of this low toxicity of PCQs, they are not toxic to most insects or to birds, animals and humans. Moreover, the toxicity level is sufficiently low that any active material that becomes leached into the soil will not be detrimental to the normal constituents of fertile soil layers.

C. Coadjuvants

As used herein, the term "coadjuvant" refers to materials which have a bio-activity different than the polycyclic quinones themselves. Such materials include fertilizers, fungicides, growth regulators, pesticides, herbicides and mixtures thereof. Both liquid and solid coadjuvants can be used in conjunction with the polycyclic quinones of the invention, depending on the manner of application. (See discussion below.) Suitable coadjuvants for use with the invention, among others, are triallate, carbofuran, phorate, terbufos, chlorpyrifos, mepiquat chloride and ethephon.

D. Additives

As used herein, the term "additives" refers to materials which augment the effectiveness of the compositions of the invention, but which do not by themselves have bio-activity. These include such materials as surfactants, wetting agents, defoaming agents, extenders, sticking agents, penetrants, plasticizers, activators, spreading agents, diluents, odorants and the like.

E. Methods of Application

In general, plant seeds can be coated with polycyclic quinones or precursors thereof by spraying on the coating or by immersing the seeds in a liquid dispersion of the polycyclic quinone or liquid solution of the precursor thereof. A particularly preferred way of coating the seeds involves the use of a "seed box" in which the seeds are stirred, while spraying on the liquid coating containing the polycyclic quinone or precursor. Fine droplets of the treating dispersion are sprayed at a rate such that the seeds remain free-flowing. The treating material can also be sprayed onto the seeds while they are fluidized in air. Both polycyclic quinones and precursors thereof can be applied in this manner. Though the seeds can be coated by immersion in the treating solution, this method is not preferred because it involves intensive drying. So long as the coating is sufficient to provide an operable amount of the particulate coating, further coating thickness is not needed.

Though it is preferred to apply the polycyclic quinone directly as a coating on the seeds, the same liquid treating solutions can render protection to the buried seeds by coating the surface of the ground overlying the seeds. However, this requires that the coating be carried out in situ, which is far less efficient than coating the seeds in bulk before planting.

In general, only small concentrations of polycyclic quinone or precursor need be applied to the seeds. For example, as little as 25 mg/m2, basis seed surface area, has been found to be effective. However, at least 50 mg/m2 is preferred. Though still higher amounts of coatings can be applied and numerous coatings can be used as well, care must be taken that the dried coating is not be thick that germination of the seed is compromised. Therefore, it is preferred that the seeds not be continuously coated in order that the coating not inhibit germination.

EXAMPLES

The objective of these examples was to determine the efficacy of the test substance (AQ) against key target bird species, including the European starling, redwinged blackbird, cowbird and American robin.

Materials and Methods

Test Substance

The test substance was an aqueous liquid formulation containing 50% wt. AQ.

Test Birds

Scientific collecting permits were obtained for the various bird species from the U.S. Fish and Wildlife Service and the Louisiana Department of Wildlife and Fisheries, Environmental Branch. Birds were collected using mist nets and modified Australian Crow traps. The species utilized included the European starling (*Sturnus vulgaris*), American robin (*Turdus migratorius*), cowbird (*Molothrus ater*), redwinged blackbird (*Agelaius Phaeniceus*), and the northern bobwhite quail (*Colinus Virginianus*). Starlings were trapped or netted from various areas of Larimer and Weld Counties, Colo. Birds were captured near cattle or sheep feedlots, in sugarcane fields, along tree lines, and in rice fields. With the exception of the bobwhite quail, all birds used in the testing were wild birds. Quail chicks were hatched from the eggs of captive bobwhites using incubators.

Housing and Maintenance of the Test Birds

Studies were conducted at a facility near Wellington, Colo. Cages for laboratory tests were 63×63×45 cm. in size. Racks on rollers contained 9 individual cages with stainless steel dividers separating the birds. Only one bird per cage was used during the research in order to obtain information on individual variations in food consumption. Each test room was equipped with automatic timers to maintain light at 12 hours light/dark. A central heating system maintained test rooms at 20°–22° C. and the relative humidity at 35–55%. Test rooms were isolated and only one species per room was allowed. Noise was kept to a minimum to avoid disturbing the captive birds.

Captive birds were fed a maintenance ration consisting of 75% Ranchway Feed Game Bird Grower, 20% whole grain millet or wheat, and 5% oyster shell grit. When birds tested in choice studies were to use millet as a carrier for the test material, the millet was included in the maintenance ration.

Laboratory Choice Tests

Starlings were used as the main laboratory test bird since the species is ubiquitous, a common problem to farming operations, and very abundant in the U.S. (approximately 600 million starlings on the continental mainland). Birds were housed in individual cages. Wild birds were allowed to condition to the test facility for approximately one week or more before being used in studies. Birds were presented treated grain and control (untreated grain) in separately marked cups in choice tests. The position of the cups was reversed daily. Studies normally lasted four days. Consumption was recorded daily to the nearest 0.1 g. Similar studies were repeated on redwinged blackbirds and robins in Louisiana. Test groups per dose level consisted of 9 or 10 starlings. All birds were adults or sub-adults (young of the year which were adult size, but had not fully come into adult plumage).

A study was conducted to determine the Discrimination Threshold, that is, the concentration at which AQ exhibits a repellency action.

A further laboratory study was completed to assess whether or not the repellency action of AQ was related to taste or odor. A feeding container was devised using a modified base for a standard 0.5 L bird waterer. The metal water receptacle contained a center portion that screwed onto water jars. The outer portion of the lid contained the area where water is available to birds. Anthraquinone-coated millet (1000 ppm) was placed in the outer portion of the lid and covered with wire mesh. Uncoated millet was provided in the center of the lid and served as the basal diet for the individually housed birds. Feed consumption was recorded after two consecutive days, with the position of the cups being reversed each day. The hypotheses tested was thus: if odor is the major role involved in repellency, then feed consumption in the feed trays treated with treated AQ-treated seed would be significantly less than the cup with the untreated seed.

Pen Studies

Repellency studies on redwinged blackbirds, cowbirds and American robins were conducted in Louisiana to determine the potential repellency on rice, millet and berries. Six 10×3.5×3M pens and one 10×3.5M pen were constructed in a secluded area among sugarcane fields. Food and water were provided ad-lib. Choice tests were employed in both individually caged birds and birds in pens. Oil field pipe and plastic netting were used to enclose the pens. An opaque cloth was placed over the top one third of the pens to protect birds from unnecessary stress induced by sunlight and rain. Perches were installed at each end of the pens to provide roosting sites and protection against bad weather.

Within the pens, 1×1M raised plots (5 cm above ground level, constructed with wood and filled with dirt) were positioned equidistant from the perimeters of the pen and a minimum of 1M apart. The number of plots varied from 4 to 10 depending on the number of birds (2 to 20) placed into the pens (redwinged blackbirds or cowbirds). From 200 to 1,000 rice seeds were placed onto the plots after appropriate preparation. Control plots received soaked rice with no AQ. After 1 to 3 exposure periods, the number of remaining seeds found were counted.

Birds were conditioned to the pens for a minimum of three days before test material was applied.

In southern Louisiana, rice farmers generally soak rice seed in water and air-dry the seeds before planting. This is to help the seed germinate before planting, to help the young plants become established sooner and thus to reduce bird damage. For studies with sprouting rice, rice was soaked for 24 hours and allowed to air-dry before use. Two types of treatment were used: (1) pre-soak, where the rice was coated with the AQ, soaked in water for 24 hours, air-dried for 24 hours and then applied to plots and (2) post-soak treatment involved soaking the rice for 24 hours, air-drying for 24 hours, coating the grains with the appropriate amount of AQ, air-drying for one hour and then applying the grains to the test plots.

For studies with grains and berries, the appropriate amount of AQ was weighed out, placed in plastic bags and mixed in the plastic bags for 5 minutes. The formulated product was then air-dried for about 30 minutes before use.

Results and Discussion

The initial studies revealed that the starlings were able to detect AQ at 151 ppm, however, the compound did not have a significant repellency effect until a higher dose was used. Results are presented in Tables 1 and 2 below. To attain 90% repellency using AQ against starlings, the concentration of AQ would have to be 1,131 ppm.

TABLE 1

Determination of Discrimination Threshold
for 9,10-Anthraquinone in European Starlings

| Test Group | 1 | 2 | 3 | 4 | 5 | |
|---|---|---|---|---|---|---|
| Nominal AQ Conc. (ppm) | 0 | 100 | 250 | 500 | 1000 | |
| Log. Conc. (x) | 0.0 | 2.0 | 2.4 | 2.7 | 3.0 | DT = 151 ppm |
| Log. Unt./Trt (y) | | | | | | |

TABLE 2

Average Daily Feed Consumption of European Starlings During
Discrimination Threshold Tests With 9,10-Anthraquinone

| Test Group | 1 | 2 | 3 | 4 | 5 |
|---|---|---|---|---|---|
| Nominal AQ Concentrations (ppm) | 0 | 100 | 250 | 500 | 1000 |
| Seed Consumption (5 lb/day) | | | | | |
| Untreated feed | 4.1 | 4.4 | 2.3 | 2.2 | 1.2 |
| Treated feed | 4.1 | 5.1 | 3.8 | 5.2 | 6.4 |
| Wt. Ratio Untreated/Treated | 50/50 | 46/54 | 38/62 | 29/71 | 16/84 |

Results of the odor test are presented in Table 3 (below). There was no difference in seed consumption between the treated and control containers. Odor, therefore, does not play a role in the repellency of AQ as measured. Observations from both the laboratory and pen studies revealed that there were no adverse effects on the behavior and health of birds used in the AQ research.

TABLE 3

Determination of Repellency Mode of Actives On Ten Adult Starlings

| Test Days | 1 | 2 | 3 | 4 |
|---|---|---|---|---|
| Average Feed Consumption(s) | | | | |
| Untreated | 7.73 | 7.20 | 6.38 | 11.07 |
| Treated | 6.54 | 7.39 | 8.13 | 4.57 |
| Total | 14.27 | 14.59 | 14.51 | 15.64 |
| Wt. Ratio Treated/ Untreated | 54.2/45.8 | 49.3/50.7 | 44.0/56.0 | 70.8/29.2 |

The results of the 5-day discrimination threshold test conducted with AQ in northern bobwhite quail chicks showed the discrimination threshold to be 1,180 ppm (Table 4). To determine the discrimination threshold, certain criteria must be met; the vehicle control group must have the same X and Y values and the X and Y values of the treatment groups should increase proportionately. The Y values, Log (untreated/treated) did not increase as the X values Log concentration increased. To determine the discrimination threshold, eight treatment levels were used: 10 ppm, 25 pm, 50 ppm, 100 ppm, 200 ppm, 400 ppm, 800 ppm, and 1600 ppm. At the 800 ppm level, there wasa marked change in the feeding habits of the chicks. This indicates that AQ at a level of 800 ppm or higher does in fact repel the birds.

TABLE 4

Determination of Discrimination Threshold of 9,10-Anthraquinone
With Corn Oil in Choice Test Using Northern Bobwhite Quail Chicks

| Group | Nominal AQ Concentrations (ppm) | Log. Conc. (x) | Log. (Untr/Tretd) (y) |
|---|---|---|---|
| Control | 0 | 0.000 | −0.504 |
| 1 | 10 | 1.000 | −0.260 |
| 2 | 25 | 1.398 | −0.346 |
| 3 | 50 | 1.699 | −0.604 |
| 4 | 100 | 2.000 | −0.521 |
| 5 | 200 | 2.301 | −0.184 |
| 6 | 400 | 2.602 | −0.382 |
| 7 | 800 | 2.903 | 0.449 |
| 8 | 1600 | 3.204 | 0.125 |

$X^{DT} = 3.072$
Antilog $X^{DT} = 1180$ ppm

Pen and cage studies conducted in Louisiana during January, 1996, revealed the potential for AQ to be used as a repellent against American robins and redwinged blackbirds (Table 5). Although the highest concentration tested was only 1000 ppm, the repellency was 60%, indicating the potential for higher repellency at higher AQ levels.

TABLE 5

Cage and Pen Studies on Louisiana Birds Fed With Fruit or Grain Treated With 9,10-Anthraquinone

| Type of Study | Target Species | Treated Food | AQ Concentration (ppm) | % Repellency |
|---|---|---|---|---|
| Cage | American Robin | Holly Berries | 53.0 | 50 |
| Cage | American Robin | Holly Berries | 52.4 | 200 |
| Cage | American Robin | Holly Berries | 33.5 | 400 |
| Cage | American Robin | Holly Berries | 51.3 | 500 |
| Cage | American Robin | Holly Berries | 60.0 | 1000 |
| Cage | Redwing Blackbird | Rice | 60.5 | 50 |
| Cage | Redwing Blackbird | Millet | 68.9 | 500 |
| Cage | Redwing Blackbird | Millet | 66.4 | 1000 |
| Pen | American Robin | Holly Berries | 68.9 | 500 |
| Pen | American Robin | Holly Berries | 64.0 | 1000 |

Subsequent studies during the summer and fall of 1996 demonstrated the efficacy of AQ in sprouting rice to repel redwinged blackbirds and brown-headed cowbirds. Table 6 presents the data for treatments at different periods, pre-soak and post-soak treatments. In both cases, AQ was shown to be potentially effective in pen situations.

TABLE 6

Pen Studies on Louisiana Birds Fed with Rice Treated With 9,10-Anthraquinone

| Species | Redwing Blackbirds | Redwing Blackbirds | Redwing Blackbirds | Redwing Blackbirds | Cow Birds | Cow Birds | Cow Birds | Cow Birds |
|---|---|---|---|---|---|---|---|---|
| Exposure Period, Days | 2 | 2 | 2 | 2 | 2 | 2 | 1 | 1 |
| Bird No's | 3 | 3 | 3 | 3 | 20 | 20 | 10 | 10 |
| Treatment | Pre | Post | Pre | Post | Post | Post | Pre | Pre |
| Seeds/Pen | 2,400 | 2,400 | 2.400 | 2.400 | 10,000 | 10,000 | 10,000 | 10,000 |
| Consumption: No Treat | 753 | 1200 | 2160 | 2129 | 4892 | 2661 | 2459 | 4590 |
| Consumption: Treated | 198 | 701 | 240 | 271 | 2105 | 1164 | 864 | 459 |
| Repellency | 79.2 | 63.1 | 90.0 | 88.7 | 69.9 | 80.0 | 74.0 | 90.1 |

Pre: Treat with AQ after soaking in water 24 hours
Post soak rice in water 24 hours, treat soaked rice with AQ and dry treated rice in air 24 hours.

Pen and field observations of bird behavior were made throughout the studies. In no situation were adverse effects or discomfort to the observed birds. In feeding on rice seeds, the birds squeezed the grain from the hull then ejected the hull from their mouths and ate only the inner grain. During this feeding activity, which maximized contact with AQ, the treated seeds did not affect the birds' behavior or induce pain. Consumption of AQ did not affect feeding behavior, in terms of grams of feed per day.

Upon completion of all studies, the test birds were released near the original point of capture. No test birds died due to exposure to the AQ. In a separate study, we found the $LD_{50}$ of AQ in northern bobwhite quail to be in excess of 2,000 mg/kg body weight.

What is claimed is:

1. A method for deterring birds from damaging planted seeds comprising applying to the seeds before planting a non-toxic solid coating material which is (1) repellent to the taste of birds and has a particle size no greater than about 50 micrometers and (2) absorbs light having a wave length within the range of 300–400 nm.

2. The method of claim 1 in which the non-toxic taste repellent is a polycyclic quinone or precursor thereof.

3. A method for deterring birds from damaging planted seeds comprising applying to the ground above the planted seeds a layer of non-toxic solid material which is (1) repellent to birds' taste and an has a particle size no greater than about 50 micrometers and (2) absorbs light having a wave length within the range of 300–400 nm.

4. The method of claim 3 in which the non-toxic solid material is a polycyclic quinone or an alkaline solution of polycyclic quinone precursor, which is converted to particulate polycyclic quinone upon exposure to air.

5. The method of claims 2 or 4 in which average particle size is less than 30 micrometers and no more than 10% by weight of the particles are larger than 50 micrometers.

6. The method of claims 2 or 4 in which the polycyclic quinone is selected from the group consisting of 9,10-anthraquinone,1,2-dihydroxy anthraquinone,1,4-dihydroxyanthraquinone,1,8-dihydroxyanthraquinone and mixtures thereof.

7. A method for applying to unplanted plant seeds a non-toxic solid material which is (1) repellent to birds' taste and has a particle size no greater than about 50 micrometer. (2) absorbs light having a wave length within the range of 300–400 nm comprising spraying an aqueous liquid dispersion of the repellent on the seeds while the seeds are undergoing agitation.

8. The method of claim 7 in which the non-toxic solid material is a polycyclic quinone or an alkaline solution of polycyclic quinone precursor, which is converted to particulate polycyclic quinone upon exposure to air.

9. The plant seed of claim 8 in which the polycyclic quinone is applied by coating the seed with a liquid aqueous alkaline solution of polycyclic quinone precursor and exposing the coating to air to evaporate the aqueous liquid and to convert the polycyclic quinone precursor to finely divided particles of water-insoluble polycyclic quinone.

10. The plant seed of claim 8 in which the polycyclic quinone is applied by coating the seed with a liquid aqueous dispersion of finely divided particles of polycyclic quinone and evaporating the aqueous liquid.

11. The method of claims 2 or 4 in which the solubility of the polycyclic quinone in water is less than 1,000 ppm.

12. The method of claims 2 or 4 in which the melting point of the polycyclic quinone is at least 150° C.

13. The method of claim 2 in which the $LD_{50}$ of the polycyclic quinone in orally administered female rats is at least 2,000 mg/kg.

14. The method of claims 2 or 4 in which the average particle size is less than 50 micrometers.

* * * * *